(12) United States Patent
Diao

(10) Patent No.: US 8,146,186 B2
(45) Date of Patent: Apr. 3, 2012

(54) METHOD AND DEVICE FOR POSITIONING PATIENTS WITH BREAST CANCER IN PRONE POSITION FOR IMAGING AND RADIOTHERAPY

(75) Inventor: Xiumin Diao, Columbia, MD (US)

(73) Assignee: Xcision Medical Systems, LLC, Columbia, MD (US)

( * ) Notice: Subject to any disclaimer, the term of this patent is extended or adjusted under 35 U.S.C. 154(b) by 412 days.

(21) Appl. No.: 12/583,781

(22) Filed: Aug. 26, 2009

(65) Prior Publication Data

US 2011/0047702 A1 Mar. 3, 2011

(51) Int. Cl.
*A61B 6/04* (2006.01)

(52) U.S. Cl. ............. 5/601; 5/735; 5/81.1 HS; 5/943; 378/37; 378/209

(58) Field of Classification Search ............. 5/601, 612, 5/81.1 HS, 735, 943, 946; 600/415; 378/37, 378/209; 108/137, 142; 248/657
See application file for complete search history.

(56) References Cited

U.S. PATENT DOCUMENTS

| | | | | |
|---|---|---|---|---|
| 3,165,630 A | * | 1/1965 | Bielat et al. | 378/37 |
| 3,293,668 A | * | 12/1966 | Auer | 5/81.1 HS |
| 3,962,736 A | * | 6/1976 | Fedele | 5/81.1 HS |
| 5,078,142 A | * | 1/1992 | Siczek et al. | 600/407 |
| 5,564,438 A | | 10/1996 | Merchant | |
| 5,609,152 A | | 3/1997 | Pellegrino | |
| 6,047,420 A | | 4/2000 | Priester | |
| 6,367,104 B1 | | 4/2002 | Galbo | |
| 6,493,417 B1 | * | 12/2002 | Baer et al. | 378/20 |
| 6,584,626 B1 | * | 7/2003 | DiRoma | 5/81.1 HS |
| 6,883,194 B2 | * | 4/2005 | Corbeil et al. | 5/601 |
| 6,922,859 B2 | * | 8/2005 | Gagnon et al. | 5/601 |
| 7,131,769 B2 | * | 11/2006 | Vezina | 378/209 |
| 7,216,383 B2 | * | 5/2007 | Heinl et al. | 5/601 |
| 7,636,967 B1 | * | 12/2009 | Stokes | 5/620 |
| 2007/0033735 A1 | | 2/2007 | Formenti | |
| 2007/0036267 A1 | | 2/2007 | Becker | |
| 2008/0043905 A1 | | 2/2008 | Hassanpourgol | |
| 2008/0201850 A1 | | 8/2008 | Brito | |
| 2009/0064413 A1 | | 3/2009 | Sliski | |
| 2010/0074400 A1 | * | 3/2010 | Sendai | 378/37 |

\* cited by examiner

*Primary Examiner* — Michael Trettel
(74) *Attorney, Agent, or Firm* — Ober, Kaler, Grimes & Shriver; Royal W. Craig

(57) ABSTRACT

A method and device for accurately easily and accurately positioning patients with breast cancer in the prone position for imaging and radiotherapy is disclosed. The device is a couch or support structure with a double-layer structure that allows relative planar motion between the two layers. To easily slide the top layer, an array of ball transfer units is embedded on the upper side of the bottom layer while the under side of the top layer has a corresponding array of bearing plates to prevent the ball transfer units from grinding into the top layer. A locking mechanism is specially designed to interlock the two layers safely when a knob handle is tightened. A frame of bars is attached to the bottom layer to constrain translation of the top layer. Each layer has two openings for the through insertion of breasts. When a patient lies in the prone position, the breast to be treated is pendent through the couch, and the untreated breast may be blocked from radiation exposure by a removable opening cover.

24 Claims, 6 Drawing Sheets

METHOD AND DEVICE FOR POSITIONING PATIENTS WITH BREAST CANCER IN PRONE POSITION FOR IMAGING AND RADIOTHERAPY

BACKGROUND OF THE INVENTION

1. Field of the Invention

The present invention generally relates to radiotherapy equipment and, more particularly, to a method and device for positioning patients with breast cancer in the prone position for imaging and radiation treatments.

2. Description of the Background

Breast cancer has become a global concern with over one million new cases reported annually. In the United States alone, the National Cancer Institute estimates that there will be about 200,000 new cases of breast cancer in 2009. Approximately twenty percent of these cases will result in fatalities.

Radiation therapy is an established method of treating patients with breast cancer especially when patients choose to conserve their breasts. When irradiating a breast, patient position bears an emerging concern. Currently most patients with breast cancer are treated in the supine (lying on the back) position, while the most sensitive and specific Magnetic Resonance Imaging (MRI) is performed in the prone (face down) position. Radiation treatment in the supine position only allows access from a few angles, and the supine position is also inferior due to the gravitational force, compressing the breast against the chest (which is compounded with large-breasted patients). In addition, breast motion resulting from breathing creates inaccuracies in locating the beam within the target volume.

Realizing the limitations of the supine position, imaging and treating patients with breast cancer from the prone position has been suggested by many researchers and physicians. With a patient lying on a patient support device or couch in the prone position, imaging or radiation therapy is implemented with the patient's breast pendent through an opening in the support device or couch. In the prone position, the breast tissue is pulled away from the chest wall by the gravitational force, which allows more access to the breast and reduces radiation exposure to the critical organs in the thorax (e.g., lung and heart). Another benefit of the breast radiation treatment in the prone position is that tumor targeting is more accurate by reducing the target motion associated with cardiac systole and respiratory movement. Many researchers have demonstrated that treating breast cancer by setting the patient in the prone position is more advantageous than in the conventional supine position.

One of the major issues of placing a patient in the prone position is that, once lying in the prone position, the patient losses the ability to move controllable distances for accurate positioning of her breast, especially when the patient is weak or overweight. When irradiating a tumor, it is very important to target it precisely. Unfortunately, due to difficulties in setting up patients in the prone position, both breast cancer screening and radiotherapy are more often performed in the supine position than in the prone position, although it more preferable to image and treat the breast in the prone position.

A number of patient positioning methods and devices have been developed in the past. U.S. Patent Application No. 20070036267 disclosed a patient positioning device to reduce skin radiation exposure when irradiating breast cancer in the prone position. The device employs a gas-filled bladder to spare the skin from receiving high radiation dose. U.S. Patent Application No. 19975609152 proposed a patient-supporting table for performing stereotactic mammographic biopsy procedures in the prone position. The table can pendently present a patient's breast in two different orientations with respect to the aperture. In U.S. Patent Application No. 20080201850, Brito et al. designed a patient positioning platform that allows a patient to lie in the prone position during breast imaging. The platform has a cushioned base to support the patient's torso and articulate head and arm rests. U.S. Patent Application No. 20070033735 provided a method and device for accurately and reproducibly positioning a patient's breast to receive radiation while the patient is in the prone position upon a radiation treatment table. The treatment table includes a generally flat patient support surface and a head positioning device. U.S. Pat. No. 5,564,438 proposed a method and apparatus for prone position radiation therapy of breast tissue. The apparatus effectively isolates the breast tissue to be irradiated from the rest of the body. U.S. Patent Application No. 20090064413 provided a patient support system to be used with a standard linear accelerator for prone position breast radiotherapy. The system allows access of the treatment beam to the breast from up to 360 degrees. U.S. Patent Application No. 20006047420 shows a head and upper body support system comprising three distinct supports. Each support has an inclined lower portion to support and lift the patient's abdomen and an upper portion to support the corresponding shoulder and the upper body. U.S. Patent Application No. 20056922859 proposed a patient positioning table for a medical procedure on a breast. The surface of the table can be adjusted to fit the shape of the patient's body. U.S. Patent Application No. 20080043905 disclosed a portable prone stereotactic mammography system for biopsies, image guided lumpectomies, and radiation treatment of breast. The system allows a physician to perform prone breast operations at any desired location. U.S. Patent Application No. 20026367104 disclosed a patient support method and apparatus for obtaining mammographic images. Using this method, the patient is placed in a left or right lateral decubitus position to present her breast to a mammography device. There are also commercially available prone breast boards or couches for facilitating breast treatments in the prone position. However, all these methods and devices cannot alleviate the difficulties in accurate patient positioning, which motivates the present invention, e.g., a novel method and device for precisely positioning patients with breast cancer in the prone position for imaging and radiation treatments.

The present invention allows easy and accurate patient setup in the prone position by using a double-layer couch with the top layer floating over the bottom layer for easily adjusting the position of the patient.

SUMMARY OF THE DISCLOSURE

It is the primary objective of the present disclosure to provide a method and device to allow easy and accurate patient setup in the prone position for breast imaging using computed tomography (CT), MRI, and radiation treatments.

It is another objective to provide a method and device as described above that includes a mechanism to facilitate easy movement of a patient in the prone position so that the patient and the patient's breast can be precisely positioned along two horizontal axes.

It is another objective to provide a method and device in the form of a couch including a thick bottom layer for strength and a thin top layer that interfaces with the patient, and a mechanism to allow the top layer of the couch to make planar movements easily and efficiently relative to the bottom layer of the couch.

It is another objective to provide a method and device as described above that includes a mechanism to interlock the two layers conveniently and safely.

It is another objective to provide a method and device as described above that includes a mechanism to block the untreated breast from receiving unnecessary radiation exposure.

It is another objective to provide a method and device as described above that includes a mechanism to constrain the motion range of the top layer of the couch.

In accordance with the foregoing objects, the present disclosure describes a radio-imaging couch comprising a thick bottom layer for strength and a thin top layer that interfaces with the patient, and a mechanism to allow the top layer of the couch to make planar movements easily and efficiently relative to the bottom layer of the couch. In an illustrative embodiment, the translation mechanism uses ball transfer units to facilitate the easy sliding motion between the top and bottom layers. More specifically, an array of hard bearing plates (titanium or other non-ferromagnetic material providing a hard surface) is embedded in the underside of the top layer, and an array of ball transfer units is embedded in the upper side of the bottom layer. The balls of the ball transfer units face up to support the top layer. For MRI imaging, such ball transfer units may employ ceramic balls and non-ferromagnetic metal housing(s). The hard bearing plates on the top layer of the couch prevent the balls of the ball transfer units from grinding into the top layer.

With the help of the ball transfer units, the top layer is able to slide on the bottom layer easily and reliably. In addition, there is a locking mechanism that interlocks the two layers safely. When the top layer is unlocked, an attendant can slide it conveniently through the locking mechanism. However, a frame of bars is attached to the bottom layer to limit sliding, and prevent the top layer from sliding away. Each layer of the couch has two openings for a breast to go through the couch, and a cover is provided to block one of the openings, allowing only one of the breasts to be pendent through the couch. The couch is preferably equipped with a comfortable pad on its top surface, and the couch is adapted for positioning patients in the prone position.

BRIEF DESCRIPTION OF THE FIGURES

Other objects, features, and advantages of the present invention will become more apparent from the following detailed description of the preferred embodiments and certain modifications thereof when taken together with the accompanying drawings in which.

DETAILED DESCRIPTION

The present disclosure is a method and device for accurate positioning of patients in the prone position for breast imaging and treatment. Using the disclosed new device, one can adjust the position of a patient in the prone position easily and accurately.

Figure 1:
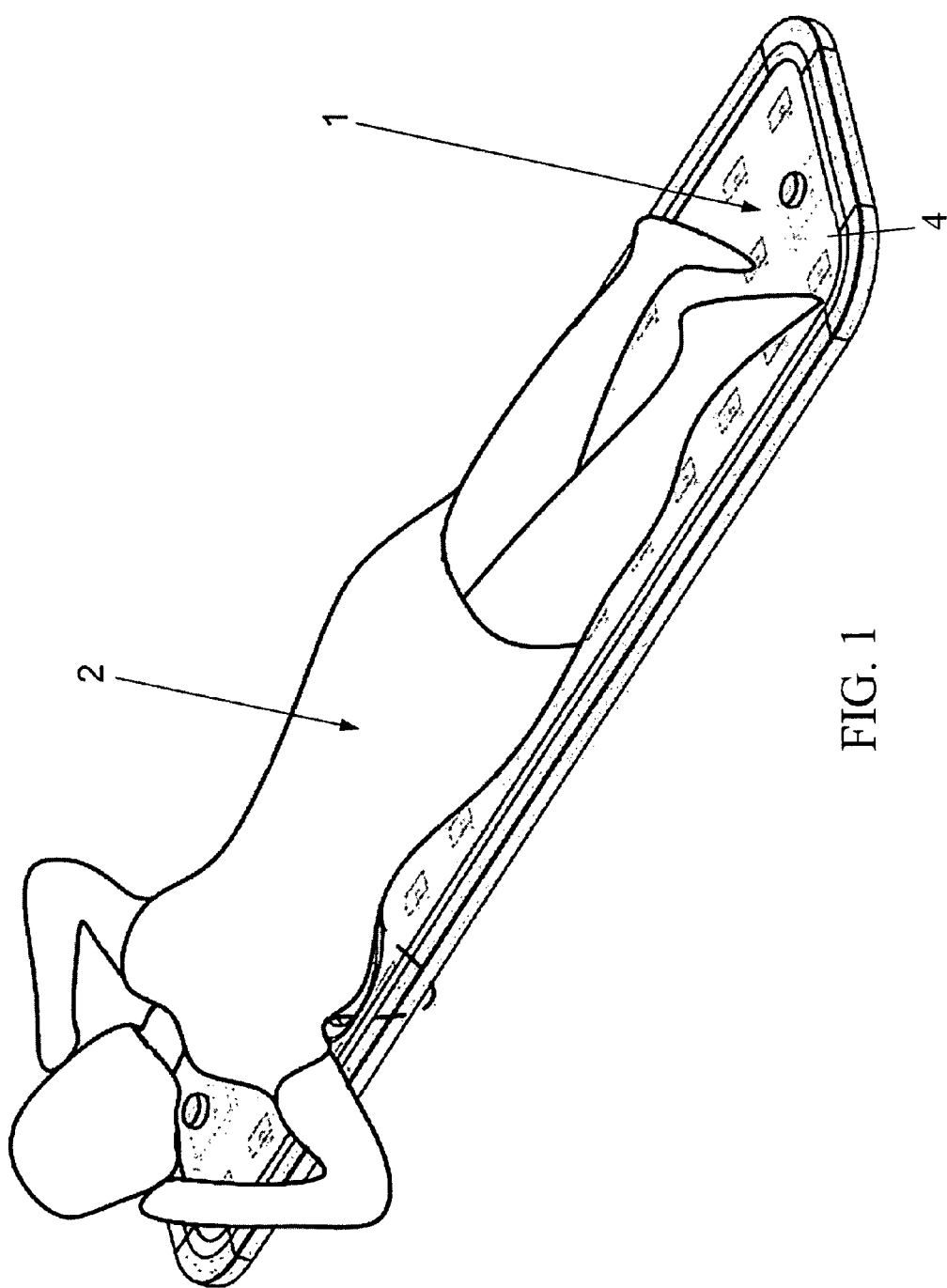
FIG. 1 is a schematic illustration of a breast cancer patient positioned on the disclosed imaging/treatment couch with a breast pendent through an opening of the couch.

Referring to FIG. 1, the patient 2 is positioned on a couch 1 comprising a top layer 4 and a bottom layer 8 (here obscured). The patient's targeted breast is pendent through an opening of the couch 1. Note that a thin mattress or pad may be put between the patient and the top of the couch for the patient's comfort.

Figure 2:
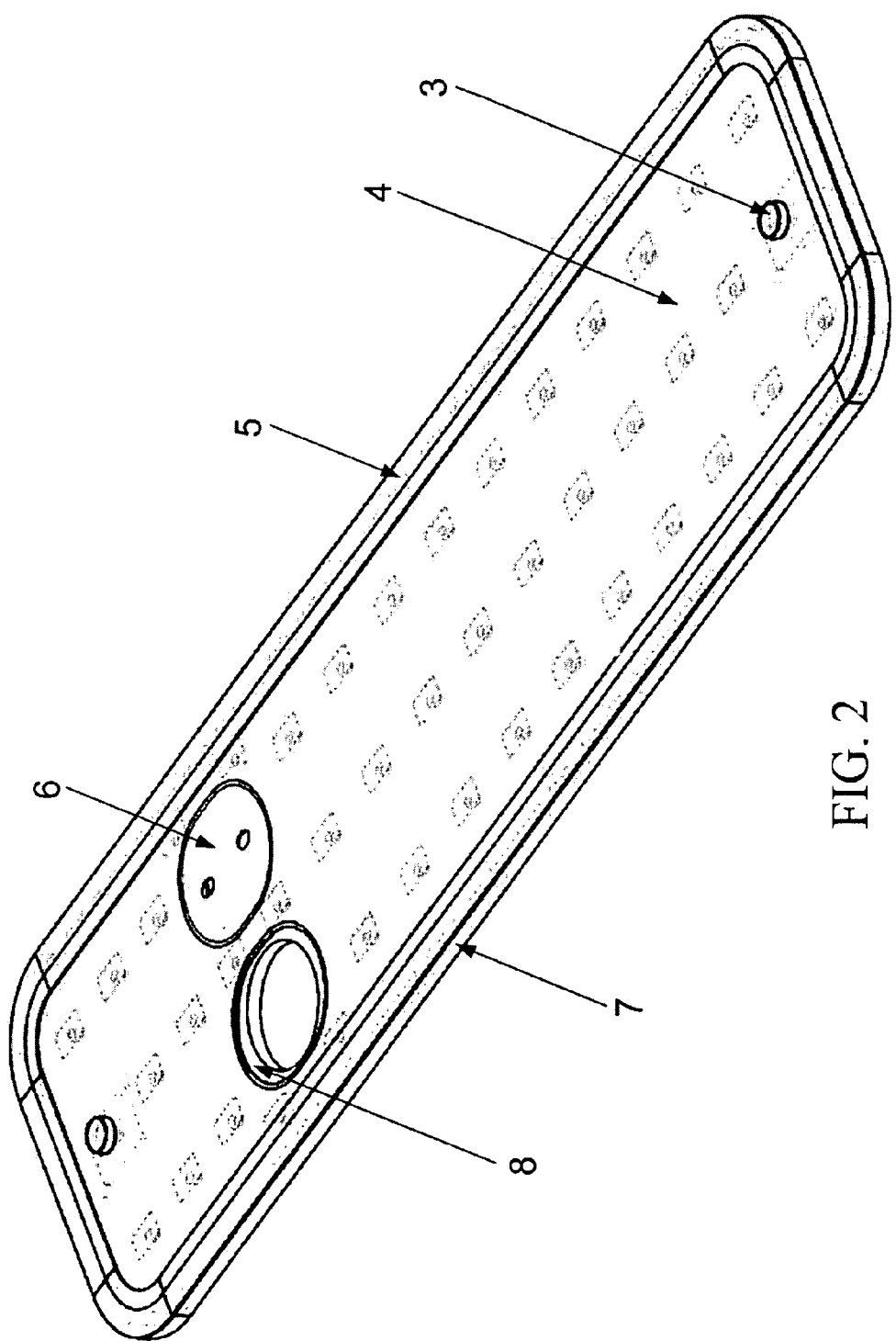
FIG. 2 is an illustration of the double-layer couch allowing the top layer to easily slide on the bottom layer.

A schematic design of the double-layer couch is illustrated in FIG. 2, including the top layer 4 and the bottom layer 8. Different materials can be used for the top and bottom layers 4, 8. For MRI imaging, the materials used for both layers should be non-ferromagnetic so that the couch will not distort the magnetic field in the imaging space. For the purpose of illustration, and as one example of the embodiment, plastic may be used for both the top and bottom layers 4, 8. The couch 1 should be strong enough to hold the patient 2. For this purpose, both the top and bottom layers should have a certain thickness. For the purpose of illustration, and as one example of an embodiment, the bottom layer 8 of the couch 1 is thicker for added strength while the top layer 4 is thinner to facilitate patient translation relative to the bottom layer.

For easy relative motion between the top and bottom layers 4, 8, a friction reduction medium is preferably used to separate the two layers. The friction reduction medium may include, but is not limited to, fluid mediums such as pressured air, lubricants, and low friction coatings on the bottom surface of the top layer or on the upper surface of the bottom layer, or various mechanical roller elements such as balls or rollers. For the purpose of illustration, and as one example of the embodiment, the embodiment disclosed herein employs an array of ball transfer units for achieving such low friction relative motion.

With ball transfer units, the patient's weight rests on the balls of the ball transfer units. To prevent the balls of the ball transfer units from cutting into the surface they roll on, the surface that the balls roll on must be very hard. As described in detail below, this may be accomplished with an array of hard plates 9 attached on the bottom side of the top layer 4 at locations corresponding to the ball transfer units embedded in the bottom layer.

Figure 3:
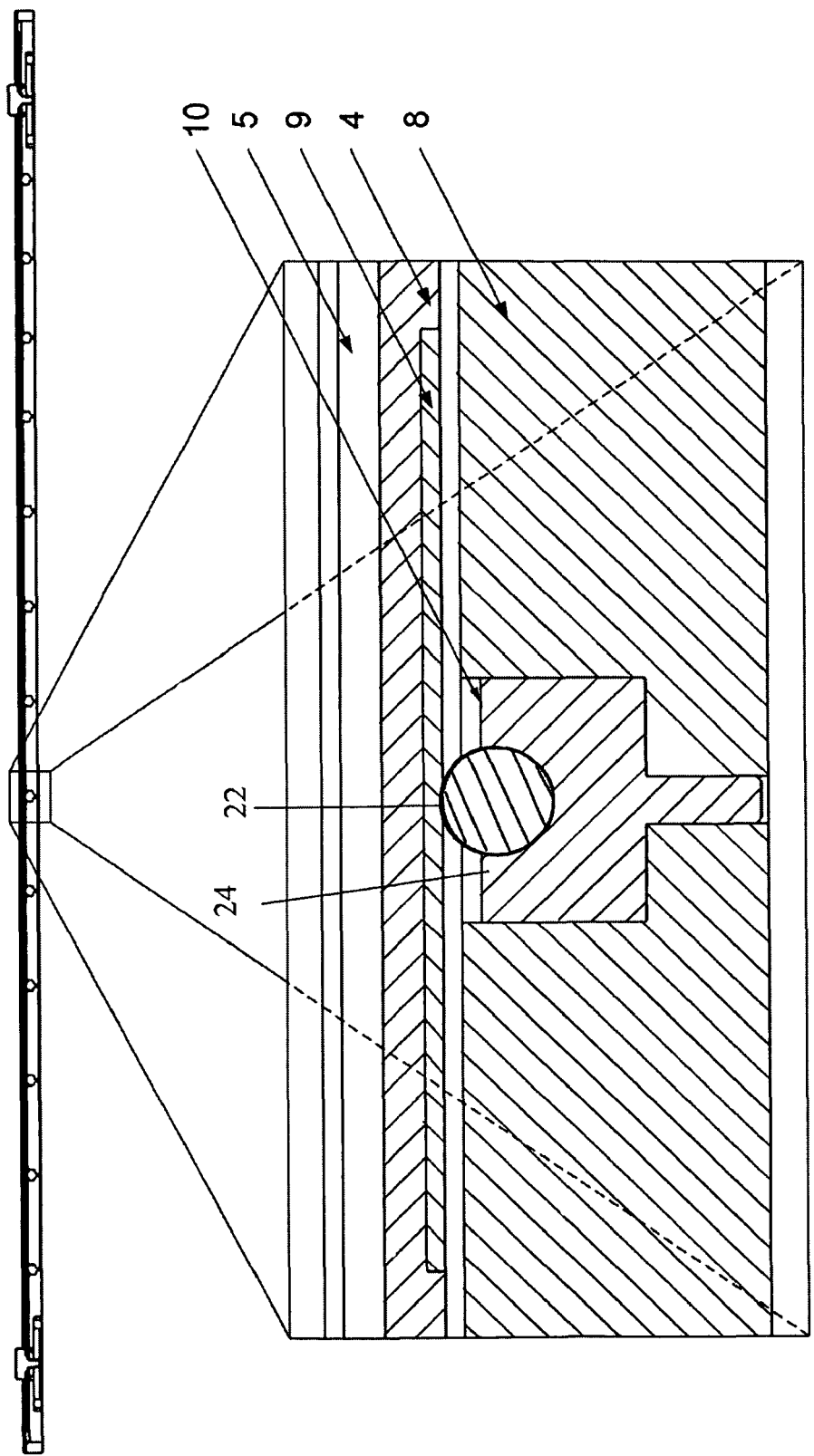
FIG. 3 is a cross section of the double-layer couch showing the ball transfer units and the hard bearing plates.

FIG. 3 is a cross section of the double-layer couch 1 showing an exemplary ball transfer unit 10 embedded in top surface of the bottom layer 8, and a corresponding hard bearing plate 9 embedded in the bottom surface of the top layer 4. The hard bearing plate 9 may comprise titanium.

Figure 4:
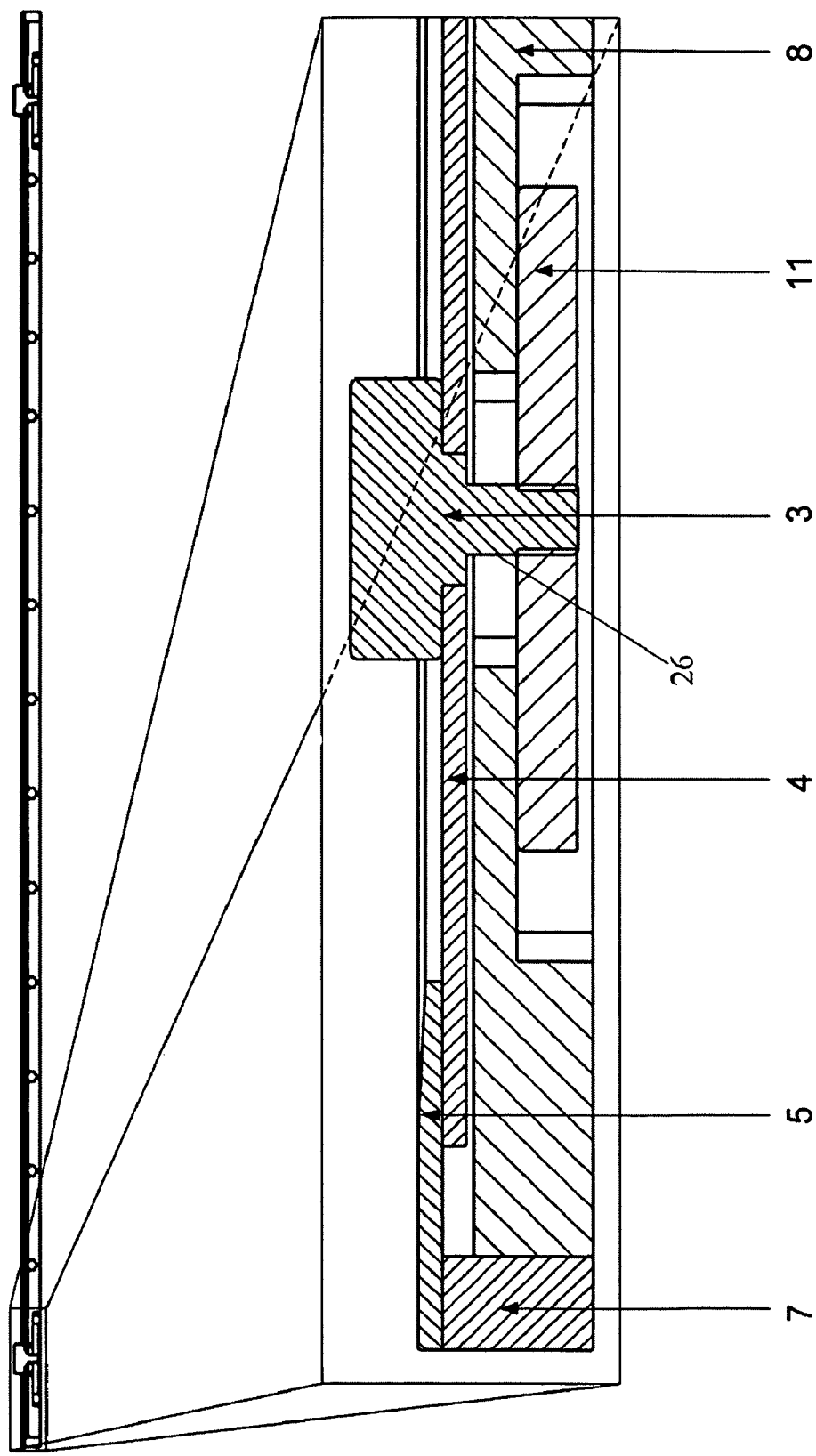
FIG. 4 is a cross section of the double-layer couch showing the locking mechanism.
Figure 5:
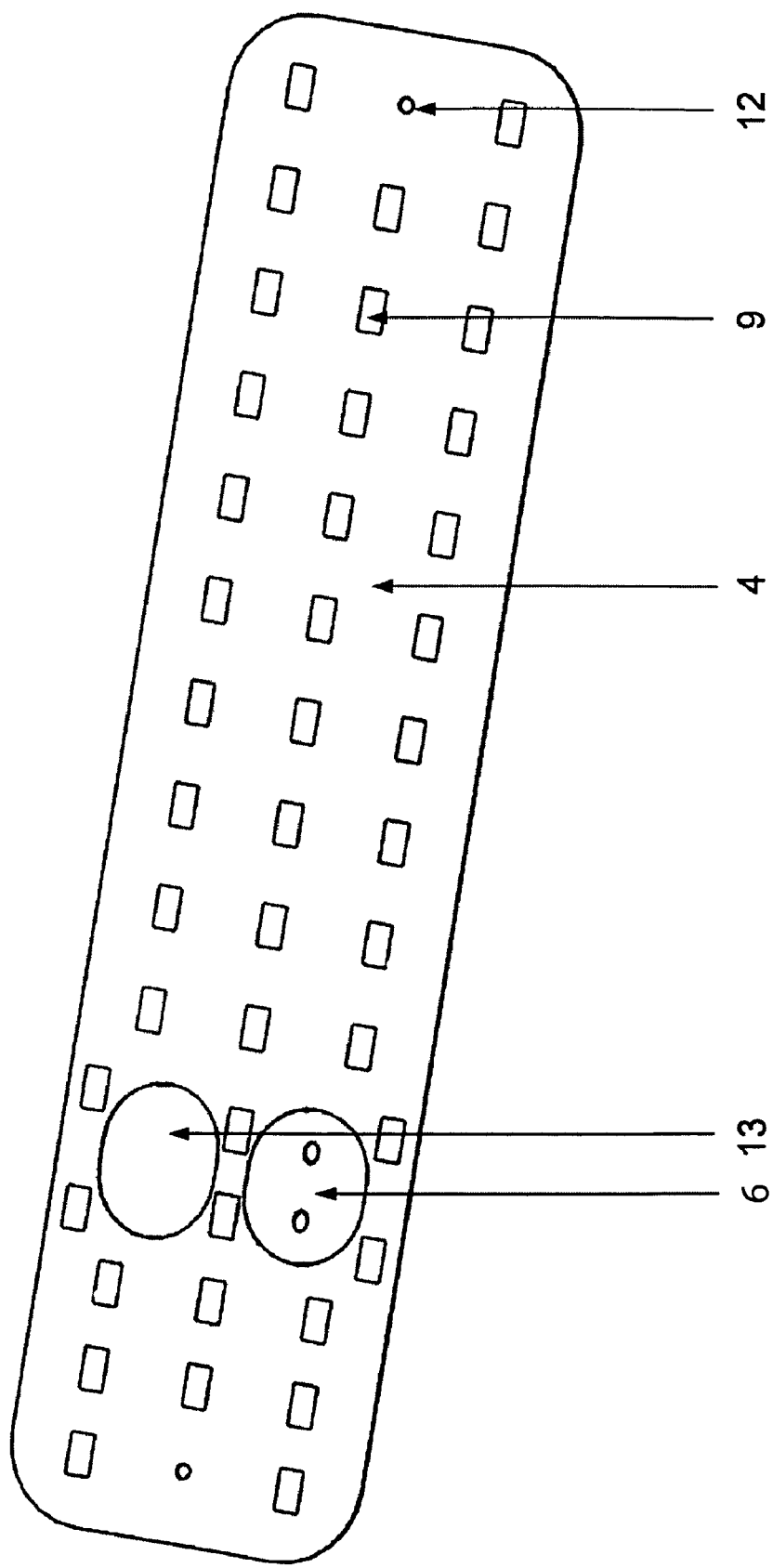
FIG. 5 is a detailed view of the under side of the top layer showing the hard bearing plates.

FIG. 5 is a detailed view of the underside of the top layer 4 showing the embedded hard bearing plates 9. As best seen in FIG. 5, the top layer 4 has an array of hard bearing plates 9 on its under side. Each bearing plate 9 is a substantially flat plate that provides a downwardly-facing bearing surface. The top layer 4 is also defined by two openings 13. The two openings 13 are uniform, and the cover 6 is interchangeable so as to selectively occlude either opening 13. In this way, cover 6 allows only one breast of the patient 2 to extend pendent through the opening 13 allowing the breast to be drawn by the force of gravity away from the patient's chest. Additionally, two small distally-positioned holes 12 on the top layer 4 are used by the locking mechanism as shown in FIG. 4.

Figure 6:
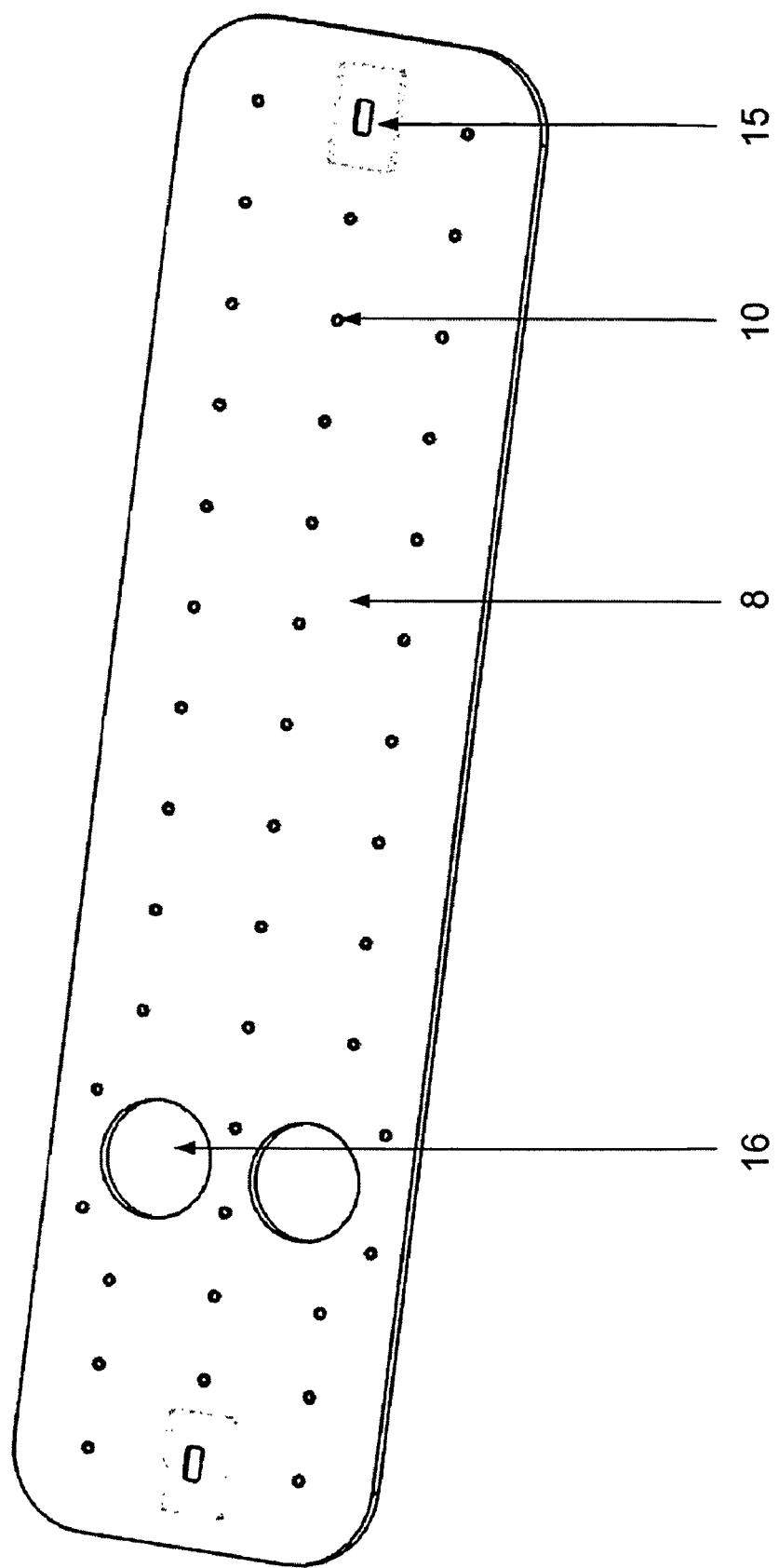
FIG. 6 is detailed view of the upper side of the bottom layer showing the embedded ball transfer units.

Now referring to FIG. 6, the bottom layer 8 has an array of ball transfer units 10, each corresponding to one of the array of bearing plates 9 on the top layer 4. The bottom layer 8 also provides two openings 16 (corresponding to openings 13 in the top layer 4) allowing the patient's breast to pendently extended. Two step holes 18 on the bottom layer 8 are used by the locking mechanism as shown in FIG. 4. The bottom layer 8 is preferably slightly larger than the top layer 4.

With collective reference to FIGS. 3 and 6, in an embodiment, each ball transfer unit 10 is radiation-transparent and further comprises a single-rolling-element bearing including, for example, a ceramic ball 22 held captive in a titanium or other non-ferromagnetic material housing 24. The ball 22 protrudes from the face of the housing 24 to provide an upwardly-facing bearing point upon which the bearing plate 9 in the top layer 4 contacts. The ball 22 is rotationally seated within the housing 24 and maintains a slight separation between the top layer 4 and bottom layer 8. The combined array of ball transfer units 10 (FIG. 6) and opposing bearing plates 9 (FIG. 5) allow the top layer 4 to slide on the bottom layer 8 easily and reliably.

FIG. 2 shows an exemplary embodiment in which a frame of peripheral restraining bars 7 is connected to the bottom layer 8. The top layer 4 is slidably inserted into the frame 7 to prevent the top layer 4 from sliding beyond the periphery of the restraining bars 7. In this example, the top layer 4 is smaller than the bottom layer 8, which leaves a gap between the periphery of the top layer 4 and the periphery of restraining bars 7. In this illustration, a cover strip 5 is provided to cover this gap, thereby improving aesthetics and sanitary conditions.

In use, the targeted breast is placed through an opening 13 or 16 in the respective top and bottom layers 4, 8, while the other breast is placed above the couch's top layer 4 supported by the cover 6. This configuration protects the untreated breast from unnecessary radiation exposure.

The couch 1 preferably has a locking mechanism to fix the relative positions of the top and bottom layers 4, 8. The locking mechanism shown in FIG. 4 interlocks the two layers 4, 8 safely. When the top layer 4 is unlocked, an attendant can slide it freely. When the top layer 4 is locked, the translational motion of the top layer 4 is constrained. The locking mechanism may be accomplished by a number of types of constraints including a pin protruding from one layer into a hole with a conforming diameter within the other layer, or an upwardly or downwardly protruding frame on either layer to keep the opposing layer captive, or by attaching interlocking bars or pins to the circumference of the top or bottom layer. One skilled in the art should understand that other suitable means may exist to achieve this locking purpose.

FIG. 4 shows one embodiment in which the two layers 4, 8 are locked together by a friction brake. In this example, the locking mechanism comprises a knob handle 3 that is accessible from above the top layer 4 turns in an integral threaded stud 26. The knob handle 3 and stud 26 pass down through both the top and bottom layers 4, 8. The threaded stud 26 engages a brake pad 11 lying beneath the bottom layer 8. Specifically, in this embodiment the knob handle 3 includes a hub that is seated in and traverses an unthreaded hole 12 on the top layer 4. The threaded stud 26 of the knob handle 3 engages a threaded hole on the brake pad 11. The brake pad 11 is embedded in the step hole 15 on the bottom layer 8 as seen in FIG. 6. This way, when the knob handle 3 is tightened, the brake pad 11 is pulled inward into contact with the bottom layer 8. When the knob handle 3 is fully tightened, the top layer 4 becomes locked to the bottom layer 8 due to the friction between the brake pad 11 and the bottom layer 8.

The couch 1 preferably also includes a mechanism that can be used to move the top layer 4 around conveniently and easily relative to the bottom layer 8. Any of a variety of knobs, pins, handgrips, or other suitable means may achieve this purpose. For the purpose of illustration, and as one example of the embodiment, the knob handle 3 of the locking mechanism may be used to move the top layer 4. When threaded stud 26 is disengaged with the threaded hole on the brake pad 11, the brake pad 11 is no longer in contact with the bottom layer 8. As a result, the locking friction between the brake pad 11 and the bottom layer 8 is eliminated. Thus, the top layer 4 may slide on the bottom layer 8 freely by moving applying force to the knob handle 3. Note that the knob handle 3 should be closely fit the hole 12 on the top layer 4, and the brake pad 11 should be smaller than the step hole 15.

A detailed view of the bearing plates 9 and the ball transfer units 10 are shown in FIG. 3. The ball transfer units 10 are installed such that their apices have the same height and are higher than the top side of the bottom layer 8. The bearing plates 9 may be embedded in conforming pockets formed on the underside of the top layer 4. The dimensions are calculated to leave a small gap between the top layer 4 and the bottom layer 8 separated by the balls 22 of the ball transfer units. The bearing plates 9 slide on the apices of the ball transfer units 10 to prevent the apices from cutting into the top layer 4. Although the illustrated embodiment has the ball transfer units 10 attached to the bottom layer 8 and the bearing plates 9 attached to the top layer 4, this orientation may be reversed—the ball transfer units 10 may be attached to the top layer 4, and the bearing plates 9 may be attached to the bottom layer 8.

It should now be apparent that the above-described device allows easy and accurate patient setup in the prone position for breast imaging and treatment, including easy movement and stabilization of a patient so that the patient and the patient's breast can be precisely positioned along two horizontal axes.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A multi-layer couch for accurately positioning patients with breast cancer in the prone position for radio imaging, comprising:
   a top layer having a top surface for supporting a patient in the prone position, a bottom surface, and a pair of holes;
   a bottom layer having a top surface and a pair of holes;
   a friction reduction mechanism between said top layer and said bottom layer for minimizing friction there between; and
   wherein said pair of holes in the top layer and said pair of holes in the bottom layer are adjacently aligned for insertion of a patient's breast.

2. The multi-layer couch for accurately positioning patients with breast cancer in the prone position for radio imaging according to claim 1, wherein said friction reduction mechanism further comprises a plurality of ball transfer units attached to said top layer or said bottom layer.

3. The multi-layer couch for accurately positioning patients with breast cancer in the prone position for radio imaging according to claim 2, wherein said plurality of ball transfer units are attached to the top surface of said bottom layer.

4. The multi-layer couch for accurately positioning patients with breast cancer in the prone position for radio imaging according to claim 2, further comprising a plurality of bearing plates attached to the other layer of said top layer or said bottom layer to which said ball transfer units are attached.

5. The multi-layer couch for accurately positioning patients with breast cancer in the prone position for radio imaging according to claim 1, further comprising a locking mechanism for selectively locking said top layer to said bottom layer to prevent relative translation.

6. The multi-layer couch for accurately positioning patients with breast cancer in the prone position for radio imaging according to claim 5, wherein said locking mechanism comprises a screw-tightened friction brake.

7. The multi-layer couch for accurately positioning patients with breast cancer in the prone position for radio imaging according to claim 1, further comprising a translation limiting mechanism for limiting relative translation of said top layer to said bottom layer.

8. The multi-layer couch for accurately positioning patients with breast cancer in the prone position for radio imaging according to claim 7, wherein said translation limiting mechanism comprises a frame of bars surrounding said bottom layer to limit relative translation of the top layer.

9. The multi-layer couch for accurately positioning patients with breast cancer in the prone position for radio imaging according to claim 1, further comprising a removable cover for selectively covering one of said pair of holes in the top layer to prevent insertion of a patient's breast.

10. A method for accurately positioning patients with breast cancer in the prone position for radio imaging, comprising the steps of:
- lying said patient on a multi-layer couch in the prone position, said multi-layer couch comprising a first layer and a second layer;
- said patient placing a breast through a hole through the first and second layers of said couch;
- adjusting said first layer of said couch relative to said second layer of said couch by relative translation between said layers; and
- locking said first layer of said couch in position relative to said second layer of said couch to prevent relative translation between said layers.

11. A double-layer support platform for positioning patients with breast cancer in the prone position for imaging and radiotherapy, comprising a top layer for patient-support slidably mounted on a bottom layer for relative translation, said top layer being defined by two adjacent openings for insertion of a patient's breast, and said bottom layer being defined by two adjacent openings corresponding to said openings in the top layer.

12. The double-layer support platform for positioning patients according to claim 11, wherein said top layer is separated from said bottom layer by a low friction medium.

13. The double-layer support platform for positioning patients according to claim 12, wherein said low friction medium comprises a plurality of ball transfer units.

14. The double-layer support platform for positioning patients according to claim 13, wherein said plurality of ball transfer units are mounted on a top side of said bottom layer.

15. The double-layer support platform for positioning patients according to claim 14, further comprising a plurality of bearing plates mounted on a bottom side of said top layer opposing said ball transfer units.

16. The double-layer support platform for positioning patients according to claim 15, wherein said plurality of bearing plates are titanium.

17. The double-layer support platform for positioning patients according to claim 13, wherein each of said plurality of ball transfer units comprises a ceramic ball held captive in a non-ferromagnetic housing, said ceramic ball protruding from said housing.

18. The double-layer support platform for positioning patients according to claim 11, wherein a patient's breast to be imaged is pendent through an opening of said pair of openings in said top layer and through a corresponding opening of said pair of openings in said bottom layer.

19. The double-layer support platform for positioning patients according to claim 18, further comprising a removable cover for selectively occluding an opening of said pair of openings in said top layer.

20. The double-layer support platform for positioning patients according to claim 11, further comprising a mechanism to constrain a range of motion of said top layer relative to said bottom layer.

21. The double-layer support platform for positioning patients according to claim 20, wherein said mechanism to constrain a range of motion comprises a frame attached to said bottom layer, said top layer being slidably inserted into the frame.

22. The double-layer support platform for positioning patients according to claim 11, further comprising a locking mechanism to selectively lock the top layer in position relative to the bottom layer.

23. The double-layer support platform for positioning patients according to claim 22, wherein said locking mechanism comprises a friction brake.

24. The double-layer support platform for positioning patients according to claim 23, wherein said friction brake is screw-tightened by a knob handle accessible from above said top layer.

* * * * *